US011305418B2

United States Patent
Luijten

(10) Patent No.: US 11,305,418 B2
(45) Date of Patent: Apr. 19, 2022

(54) EXOSKELETON GLOVE

(71) Applicant: Adjuvo Motion B.V., Delft (NL)

(72) Inventor: Johannes Luijten, Delft (NL)

(73) Assignee: Adjuvo Motion B.V., Delft (NL)

( * ) Notice: Subject to any disclaimer, the term of this patent is extended or adjusted under 35 U.S.C. 154(b) by 433 days.

(21) Appl. No.: 16/257,845

(22) Filed: Jan. 25, 2019

(65) Prior Publication Data

US 2019/0152049 A1 May 23, 2019

Related U.S. Application Data

(63) Continuation of application No. PCT/NL2017/050499, filed on Jul. 24, 2017.

(30) Foreign Application Priority Data

Jul. 25, 2016 (NL) .................................. 2017228

(51) Int. Cl.
*A61H 1/02* (2006.01)
*A63B 23/16* (2006.01)
(Continued)

(52) U.S. Cl.
CPC ............. *B25J 9/0006* (2013.01); *A61B 5/225* (2013.01); *A61H 1/0285* (2013.01);
(Continued)

(58) Field of Classification Search
CPC ...... A61H 1/02; A61H 1/0285; A61H 1/0288; A61H 2201/165; A61H 2205/065;
(Continued)

(56) References Cited

U.S. PATENT DOCUMENTS 3,756,222 A * 9/1973 Ketchum ............. A61H 1/0288
601/40
4,167,044 A * 9/1979 Girard ....................... A61F 2/72
602/20

(Continued)

FOREIGN PATENT DOCUMENTS

CN 103692454 4/2014
EP 2345951 7/2011
(Continued)

OTHER PUBLICATIONS

Ates, Serdar, "Combined Active Wrist and Hand Orthosis for Home Use: Lessons Learned", 2015 IEEE International Conference on Rehabilitation Robotics (ICORR), 2015, 398-403.

*Primary Examiner* — Tu A Vo
*Assistant Examiner* — Christopher E Miller
(74) *Attorney, Agent, or Firm* — Peacock Law P.C.; Justin Muehlmeyer

(57) ABSTRACT

An individual linkage mechanism for a finger of an exoskeleton glove with sections that are interconnected with joints to enable changing their mutual angular orientation, which linkage mechanism includes a first linkage attached to the glove, a second linkage connected to the first linkage through a first joint, a third linkage connected to the second linkage through a second joint, and a fourth linkage connected to the third linkage through a third joint, wherein the fourth linkage is provided with a finger orthosis, and the second linkage, the third linkage and the fourth linkage are capable to assume a mutually parallel placement wherein the finger orthosis is adjacent to the second joint at a farthest end from the glove, and the third joint is closer to the glove than the second joint.

10 Claims, 10 Drawing Sheets

(51) Int. Cl.
*B25J 9/00* (2006.01)
*B25J 13/02* (2006.01)
*A61B 5/22* (2006.01)
*A63B 21/00* (2006.01)
*G06F 3/01* (2006.01)

(52) U.S. Cl.
CPC ..... *A61H 1/0288* (2013.01); *A63B 21/00181* (2013.01); *A63B 23/16* (2013.01); *B25J 13/02* (2013.01); *A61H 2201/0192* (2013.01); *A61H 2201/1436* (2013.01); *A61H 2201/165* (2013.01); *A61H 2201/1635* (2013.01); *A61H 2201/1638* (2013.01); *A61H 2201/1657* (2013.01); *A61H 2201/1676* (2013.01); *A61H 2201/5069* (2013.01); *A61H 2205/067* (2013.01); *A63B 21/4019* (2015.10); *A63B 2230/605* (2013.01); *G06F 3/014* (2013.01)

(58) Field of Classification Search
CPC ........ A61H 2205/067; A63B 21/00178; A63B 23/16; B25J 9/0006; B25J 13/02
See application file for complete search history.

(56) References Cited

U.S. PATENT DOCUMENTS

| | | | | |
|---|---|---|---|---|
| 5,697,892 A * | 12/1997 | Torgerson | ............ | A61H 1/0288 601/40 |
| 6,042,555 A | 3/2000 | Kramer et al. | | |
| 6,063,087 A * | 5/2000 | Agee | ................. | A61B 17/6425 602/21 |
| 6,110,130 A * | 8/2000 | Kramer | ................ | A61B 5/1071 600/587 |
| 6,565,563 B1 * | 5/2003 | Agee | ................. | A61B 17/6425 602/21 |
| 6,592,584 B2 * | 7/2003 | Agee | ................. | A61B 17/6425 606/54 |
| 8,668,659 B2 * | 3/2014 | Kawakami | ............. | A61F 5/013 601/40 |
| 10,423,227 B2 * | 9/2019 | Gu | ........................... | G06F 3/014 |
| 10,551,927 B2 * | 2/2020 | Bae | ...................... | A61H 1/0288 |
| 2005/0273027 A1 * | 12/2005 | Farrell | ................... | A63B 23/16 602/21 |
| 2010/0305717 A1 | 12/2010 | Tong et al. | | |
| 2012/0059290 A1 * | 3/2012 | Yip | ...................... | A61H 1/0288 601/40 |
| 2012/0059291 A1 * | 3/2012 | Nguyen | ............... | A61H 1/0288 601/40 |
| 2013/0219585 A1 | 8/2013 | Bergelin et al. | | |
| 2013/0226350 A1 * | 8/2013 | Bergelin | ............. | A61H 1/0288 700/275 |
| 2013/0261514 A1 * | 10/2013 | Tsui | ..................... | A61H 1/0288 601/40 |
| 2014/0142483 A1 * | 5/2014 | Jackson, Jr. | ............. | A61F 5/013 602/16 |
| 2014/0277582 A1 * | 9/2014 | Leuthardt | ................. | A61F 2/54 623/25 |
| 2015/0223959 A1 * | 8/2015 | Cempini | ................. | A61F 5/013 602/22 |
| 2015/0245972 A1 * | 9/2015 | Arakawa | ............... | A61H 1/0288 601/40 |
| 2015/0342818 A1 * | 12/2015 | Ikebe | ................... | A61H 1/0288 601/40 |
| 2015/0374575 A1 * | 12/2015 | Kamper | ............... | A61H 1/0288 601/40 |
| 2016/0015590 A1 * | 1/2016 | Arata | ................... | A61H 1/0288 623/64 |
| 2016/0018892 A1 | 1/2016 | Gu | | |
| 2017/0071272 A1 | 3/2017 | Carey et al. | | |
| 2017/0168565 A1 * | 6/2017 | Cohen | ................. | A61B 5/0022 |

FOREIGN PATENT DOCUMENTS

| | | |
|---|---|---|
| JP | 2002-345861 | 12/2002 |
| JP | 2007-020617 | 2/2007 |
| JP | 2007-275486 | 10/2007 |
| WO | 99/21478 | 5/1999 |
| WO | 2011/054983 | 5/2011 |
| WO | 2018/021909 | 2/2018 |
| WO | 2019/221604 | 11/2019 |

* cited by examiner

EXOSKELETON GLOVE

CROSS-REFERENCE TO RELATED APPLICATIONS

This application is a continuation application of International Application No. PCT/NL2017/050499, entitled "Exoskeleton Glove", filed on Jul. 24, 2017, which claims priority to and the benefit of Netherlands Application No. 2017228, entitled "Exoskeleton Glove" filed on Jul. 25, 2016, and the specification and claims thereof are incorporated herein by reference.

STATEMENT REGARDING FEDERALLY SPONSORED RESEARCH OR DEVELOPMENT

Not Applicable.

THE NAMES OF PARTIES TO A JOINT RESEARCH AGREEMENT

Not Applicable.

INCORPORATION BY REFERENCE OF MATERIAL SUBMITTED ON A COMPACT DISC

Not Applicable.

STATEMENT REGARDING PRIOR DISCLOSURES BY THE INVENTOR OR A JOINT INVENTOR

Not Applicable.

Copyrighted Material

Not Applicable.

BACKGROUND OF THE INVENTION

Field of the Invention (Technical Field)

The invention relates to an exoskeleton glove at least provided with an individual linkage mechanism for each finger, wherein the linkage mechanism comprises sections that are interconnected with joints to enable changing their mutual angular orientation.

Description of Related Art Including Information Disclosed Under 37 C.F.R. §§ 1.97 and 1.98

Such an exoskeleton glove is known from the article *Combined Active Wrist and Hand Orthosis for Home Use: Lessons Learned,* 2015 IEEE International Conference on Rehabilitation Robotics (ICORR), pages 398-403, and available through the Internet through the following link: world wide web at researchgate.net/pubication/282667034_Combined_Active_Wist_and_Hand_Orthosis_for_Home_Use.

BRIEF SUMMARY OF THE INVENTION

The invention has as a first object to simplify the design of the exoskeleton glove, and make it less heavy and less costly.

The invention further aims to provide a solution for the problem that donning and doffing of an exoskeleton glove is often time consuming and specialized work due to potential misalignment that is prawn to occur.

The invention has as a further object to provide a construction of the exoskeleton glove which automatically prevents harmful hyperextension of the fingers of the user.

The exoskeleton glove of the invention has the features of one or more of the appended claims.

In a first aspect of the invention the linkage mechanism comprises a first linkage attached to the glove, a second linkage connected to the first linkage through a first joint, a third linkage connected to the second linkage through a second joint, and a fourth linkage connected to the third linkage through a third joint, wherein the fourth linkage is provided with a finger orthosis, and the second linkage, the third linkage and the fourth linkage are capable to assume a mutually parallel placement wherein the finger orthosis is adjacent to the second joint at a farthest end from the glove, and the third joint is closer to the glove than the second joint. This construction ensures that undesired hyperextension of the fingers is avoided, and is less complicated and heavy than the prior art solution.

Preferably the second linkage is extendable. This makes donning and doffing of the exoskeleton glove easy. Suitably this can be arranged by providing that the second linkage has a first portion which is embodied with a slide, and a second portion which is provided with a slider that is movable in the slide so as to arrange that the linkage mechanism is capable to be attuned to a user's finger length.

It is preferred that the slider is lockable in the slide to fixate the glove to the dimensions of a user's hand and fingers.

Advantageously the first joint and/or the second joint is provided with a sensor for measuring angular displacement of the linkages connected to said joints. Such sensors can beneficially be used to monitor the use of the glove.

Beneficially the first joint and/or the second joint is spring-loaded for resisting or supporting angular displacement of the linkages connected to said joints.

It is further preferred that the glove is provided with an individual linkage mechanism for a thumb, wherein in addition to the individual linkage mechanism for each finger, the linkage mechanism for the thumb is provided with an intermediate linkage or linkages between the first linkage and the glove that indirectly attaches the first linkage to the glove.

Preferably the intermediate linkage or linkages are provided with one or more joints to enable movements of the linkage mechanism for the thumb according to a user's carpalmetacarpal joint. Clearly this promotes the use of the exoskeleton glove of the invention for rehabilitation purposes.

The invention will hereinafter be further elucidated with reference to the drawing of an exemplary embodiment of an exoskeleton glove according to the invention and its use that is not limiting as to the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

Whenever in the figures the same reference numerals are applied, these numerals refer to the same parts.

DETAILED DESCRIPTION OF THE INVENTION

Figure 1B:
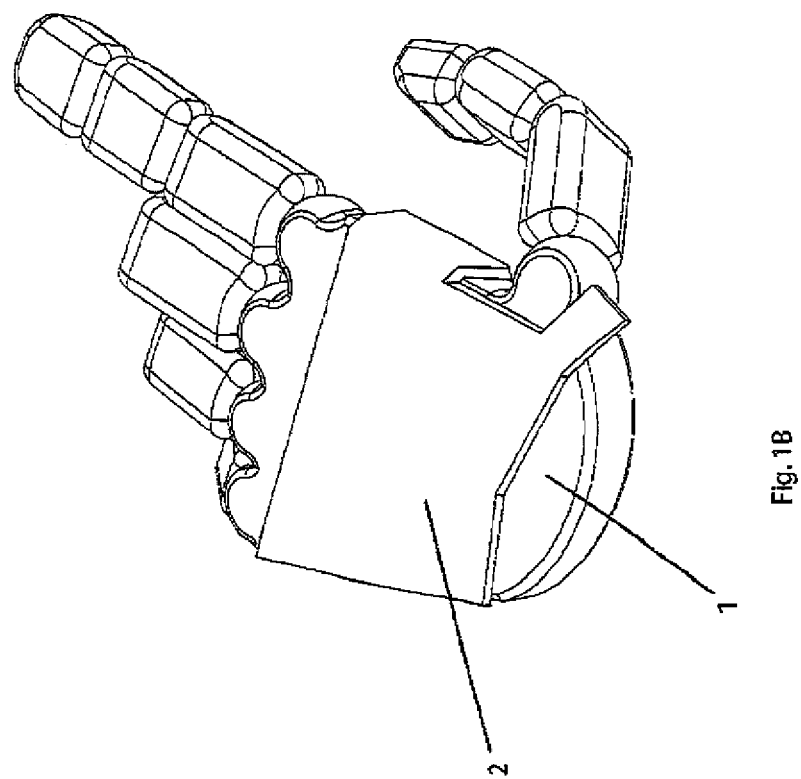
FIG. 1A and FIG. 1B illustrate an embodiment, in different perspectives, a glove of an exoskeleton glove provided on a hand of the user.
Figure 1A:
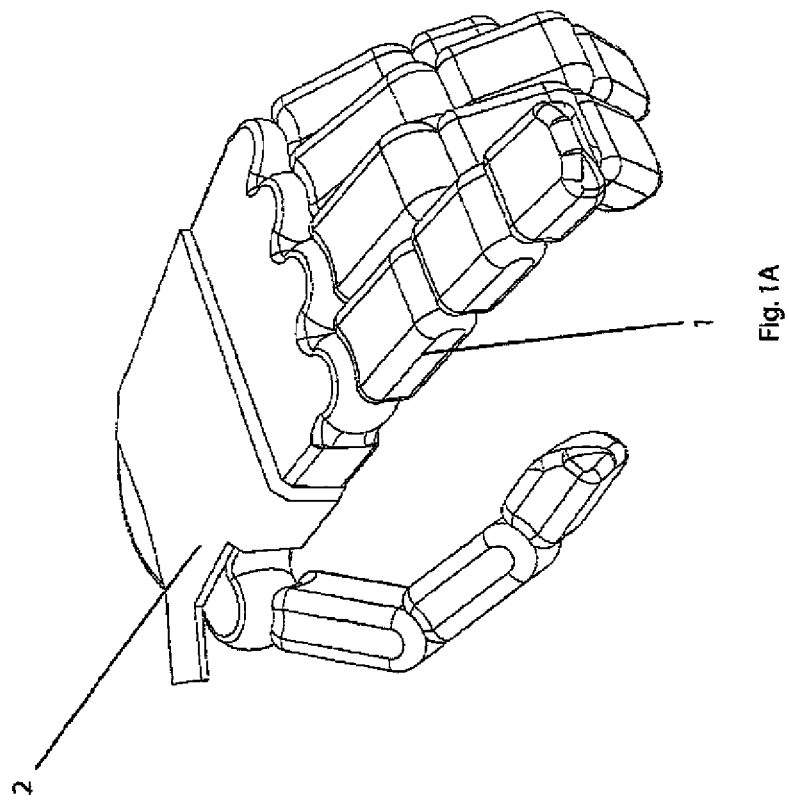
Figure 2B:
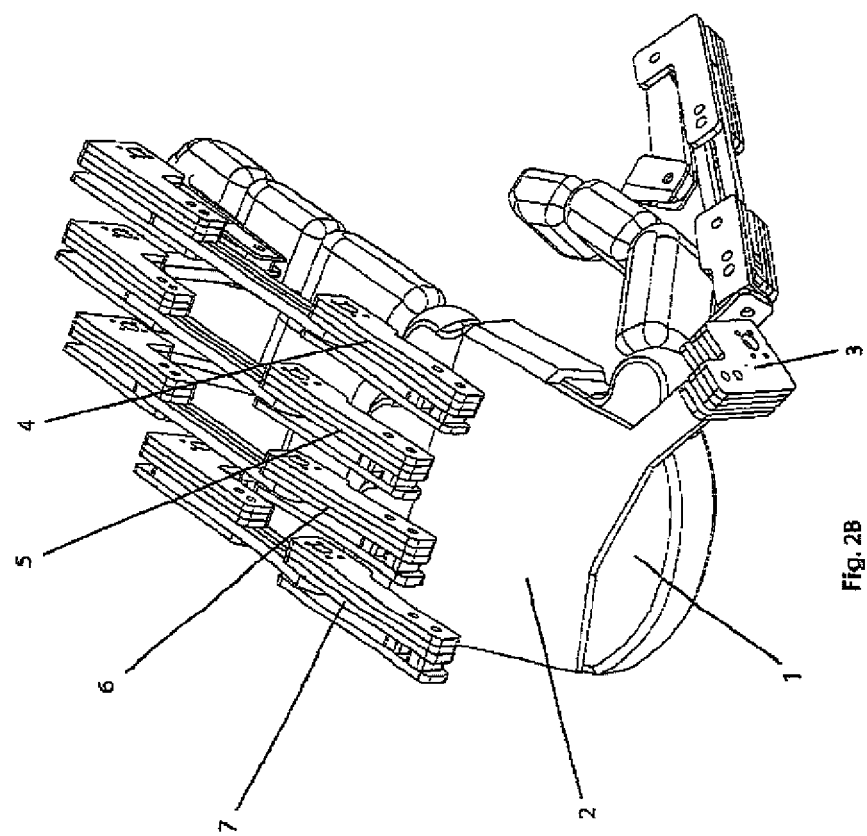
FIGS. 2A and 2B illustrate an embodiment of the individual linkage mechanisms of the thumb and the fingers in different perspectives.
Figure 2A:
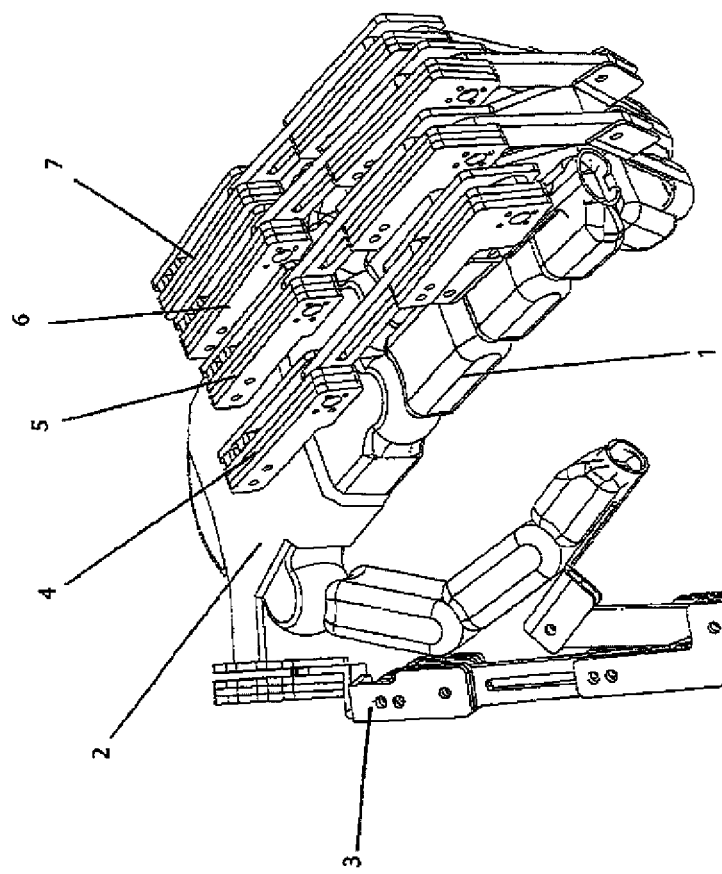

Embodiments illustrated in FIG. 1A and FIG. 1B show in different perspectives a user's hand 1 provided with a glove 2 of the exoskeleton glove which is shown in more detail in FIG. 2A and FIG. 2B.

In FIG. 2A and FIG. 2B it is shown that the exoskeleton glove is provided with an individual linkage mechanism for each finger and for the thumb. It shows a linkage mechanism 3 for the thumb, and further there are a linkage mechanism 4 for the index finger, a linkage mechanism 5 for the middle finger, a linkage mechanism 6 for the ring finger, and a linkage mechanism 7 for the small finger. The linkage mechanism 3 for the thumb is a bit more complicated than the linkage mechanisms for the fingers, as will be explained hereinafter. The construction of the linkage mechanisms for the fingers is however for each finger the same; therefore these linkage mechanisms will now hereinafter be explained only with reference to the linkage mechanism for the index finger.

Figure 3:
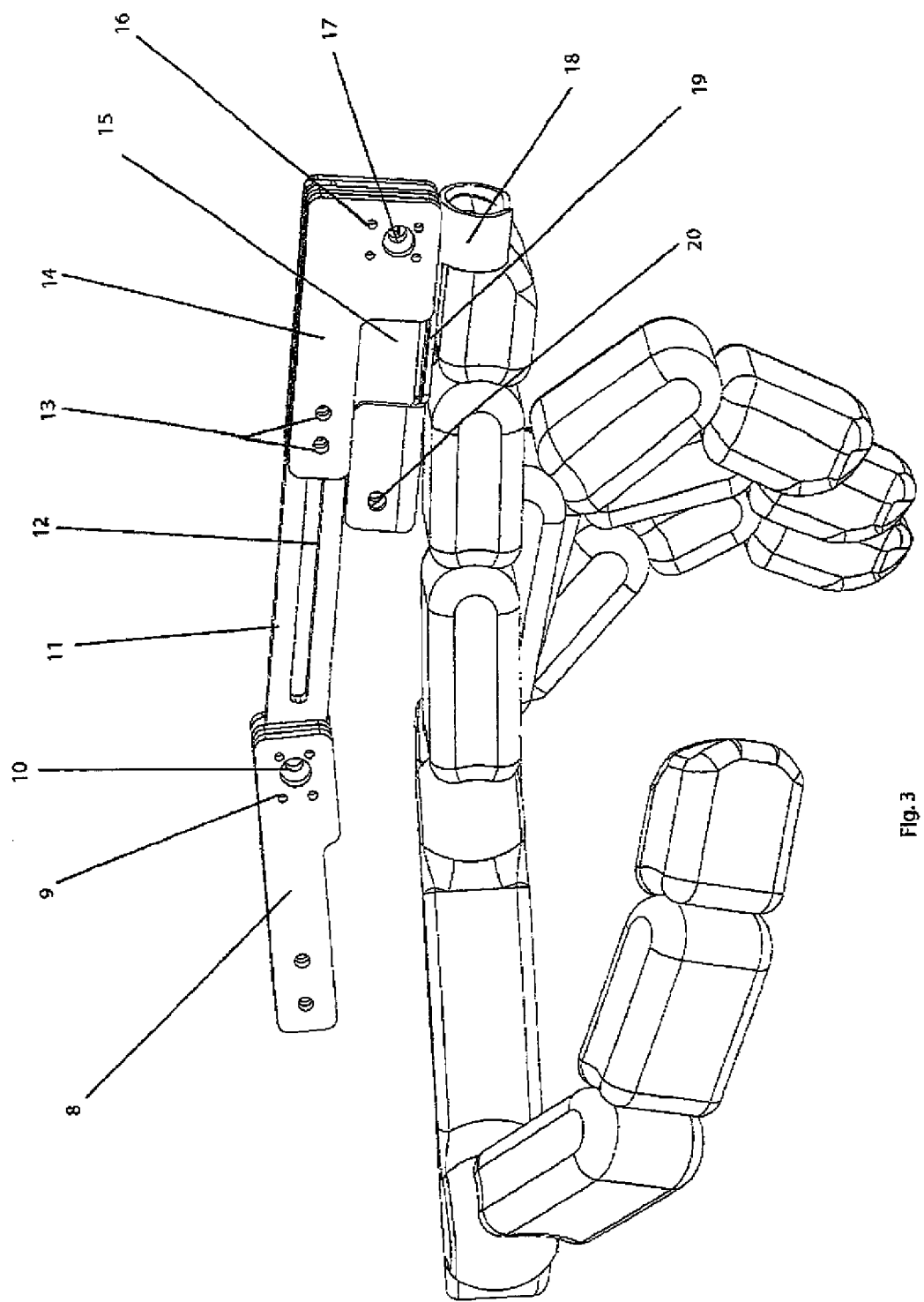
FIG. 3 illustrates an embodiment of the linkage mechanism for the index finger in a first embodiment.

FIG. 3 shows the linkage mechanism for the index finger which comprises several sections that are interconnected with joints to enable changing their mutual angular orientation. The linkage mechanism comprises a first linkage 8 attached to the glove 2, a second linkage 11, 14 connected to the first linkage 8 through a first joint 10, a third linkage 15 connected to the second linkage 11, 14 through a second joint 17, and a fourth linkage 19 connected to the third linkage 15 through a third joint 20, wherein the fourth linkage 19 is provided with a finger orthosis 18. In this construction according to the invention the second linkage 11, 14, the third linkage 15 and the fourth linkage 19 are capable to assume a mutually parallel placement wherein the finger orthosis 18 is adjacent to the second joint 17 at a farthest end from the glove 2, and the third joint 20 is closer to the glove 2 than the second joint 17.

One further feature of the invention is that the second linkage 11, 14 is extendable. For that purpose FIG. 3 shows the preferred embodiment in which the second linkage has a first portion 11 which is embodied with a slide 12, and a second portion 14 which is provided with a slider 13 that is movable in the slide 12 so as to arrange that the entire linkage mechanism is capable to be attuned to a user's finger length. It is preferred that the slider 13 is lockable in the slide 12.

FIG. 3 further shows that the first joint 10 is provided with a sensor 9 and the second joint 17 is provided with a sensor 16 for measuring angular displacement of the linkages connected to said joints 10, 17. For joint 10 this means that sensor 9 can measure the angular displacement between the first linkage 8 and the second linkage 11, 14. For joint 17 this means that sensor 16 can measure the angular displacement between the second linkage 11, 14 and the third linkage 15.

Figure 4:
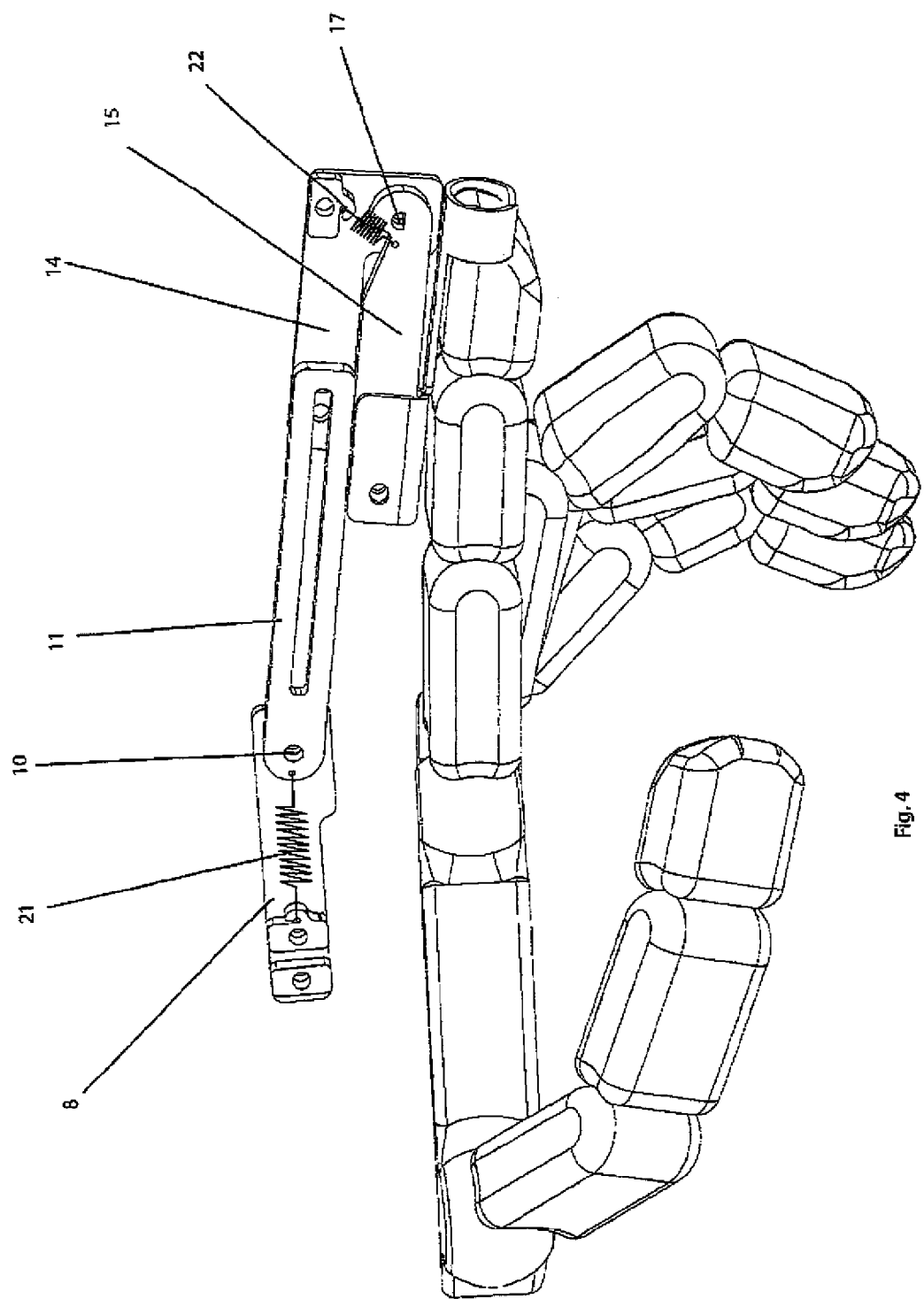
FIG. 4 illustrates an embodiment of the linkage mechanism for the index finger in a second embodiment.

FIG. 4 shows another embodiment in which the first joint 10 and the second joint 17 are spring-loaded with springs 21, 22 for resisting or supporting angular displacement of the linkages connected to said joints 10, 17. These are the same linkages as earlier mentioned, notably for joint 10 it are the first linkage 8 and the second linkage 11, 14 and for joint 17 it relates to the second linkage 11, 14 and the third linkage 15.

Figure 5:
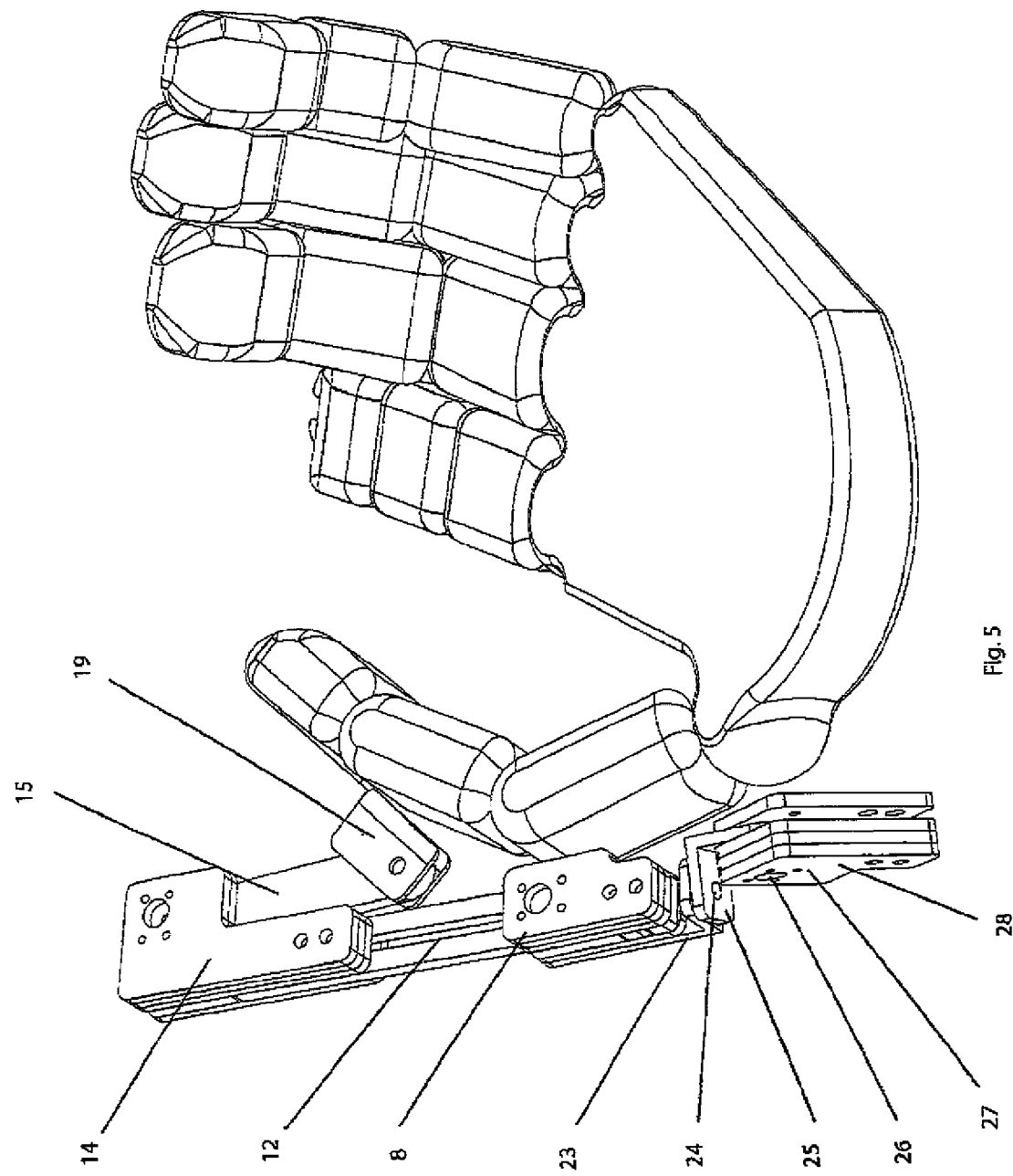
FIG. 5 illustrates an embodiment of the linkage mechanism for the thumb.

FIG. 5 shows that the exoskeleton glove is further provided with an individual linkage mechanism for a thumb, wherein in addition to the individual linkage mechanism for each finger, the linkage mechanism for the thumb is provided with an intermediate linkage or linkages 23, 25, 28 between the first linkage 8 and the glove 2 that indirectly attaches the first linkage 8 to the glove 2. The intermediate linkage or linkages 23, 25, 28 are provided with one or more joints 24, 26 to enable movements of the linkage mechanism for the thumb according to a user's carpalmetacarpal joint. Further FIG. 5 shows the presence of an additional sensor 27 for measuring angular displacement of linkage 28 with reference to linkage 25.

Finally for illustrative purposes FIGS. 6-10 show the movement of the linkage mechanism during bending of the index finger.

Figure 6:
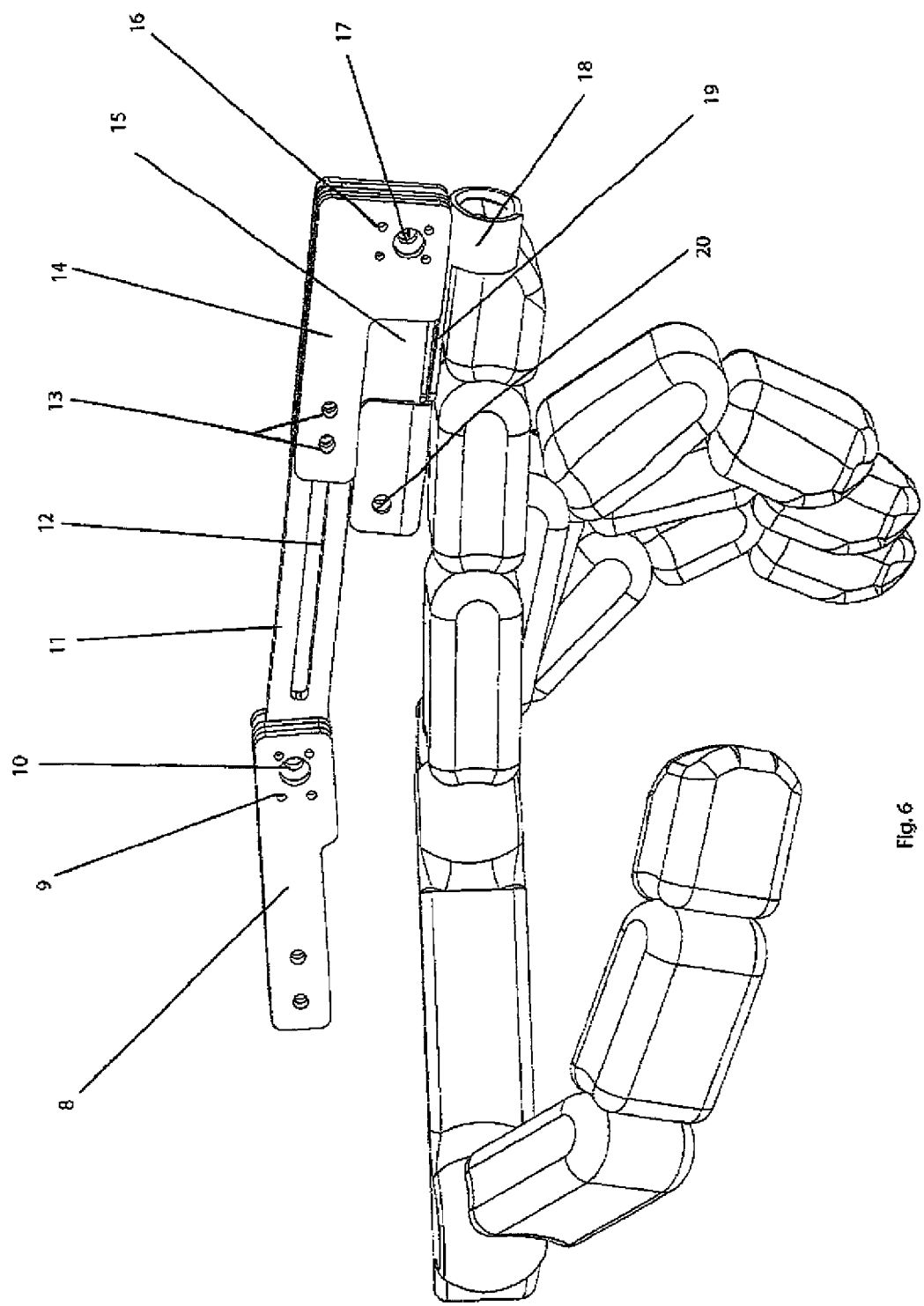
FIGS. 6-10 illustrates an embodiment of the relative movement of the linkages of the linkage mechanism of the index finger during bending.
Figure 7:
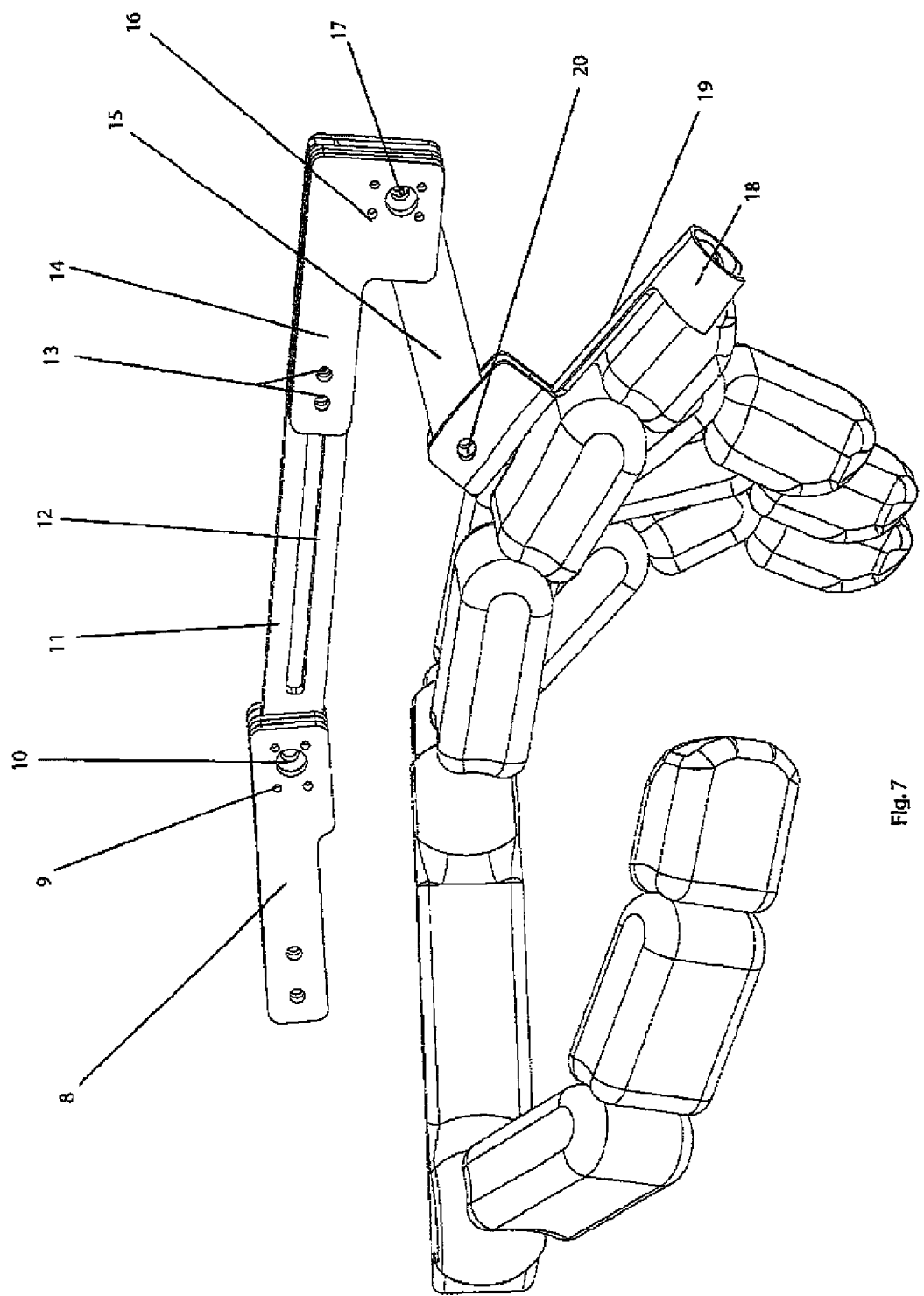

In FIG. 6 the index finger is in the extended position, and in the following FIGS. 7-10, the index finger is bent. Accordingly FIG. 7 shows that initially the parallel position of the second linkage 11, 14, the third linkage 15, and the fourth linkage 19 as assumed in FIG. 6 is left, wherein these linkages are rotated over part of a circle as enabled by the second joint 17 and the third joint 20. During this movement the first linkage 8 and the second linkage 11, 14 still more or less maintain their original angular orientation as shown in FIG. 6.

Figure 8:
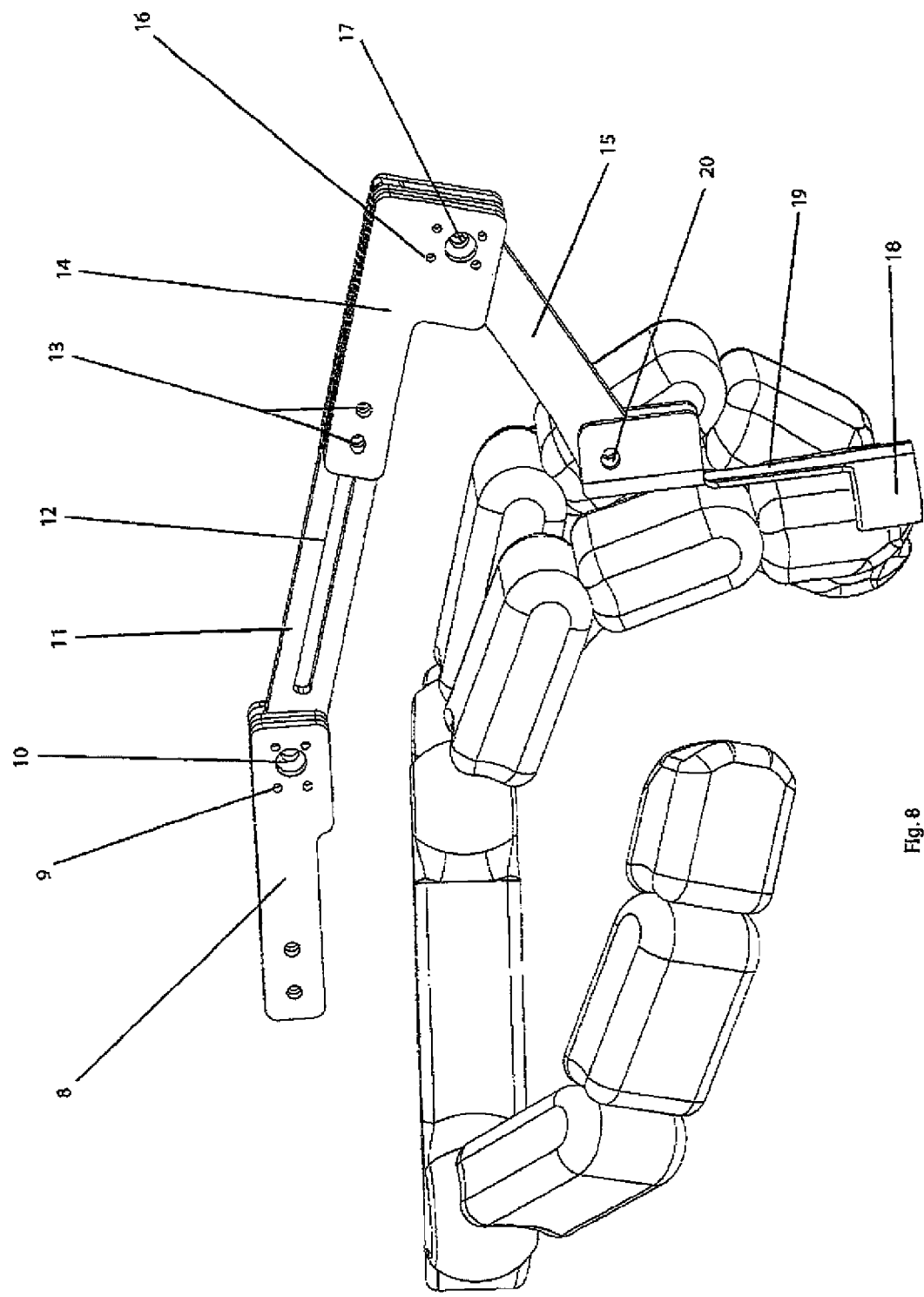
Figure 9:
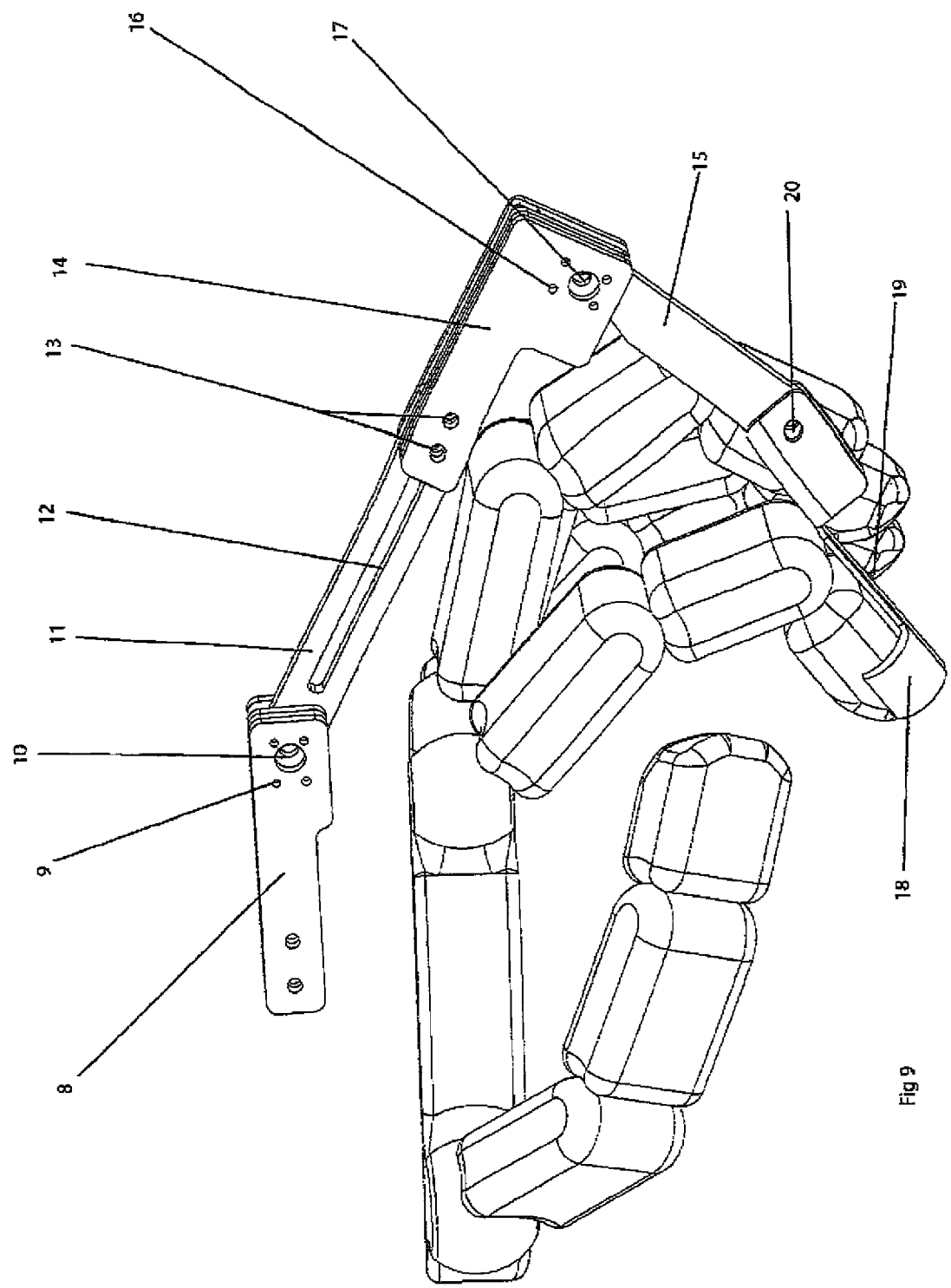
Figure 10:
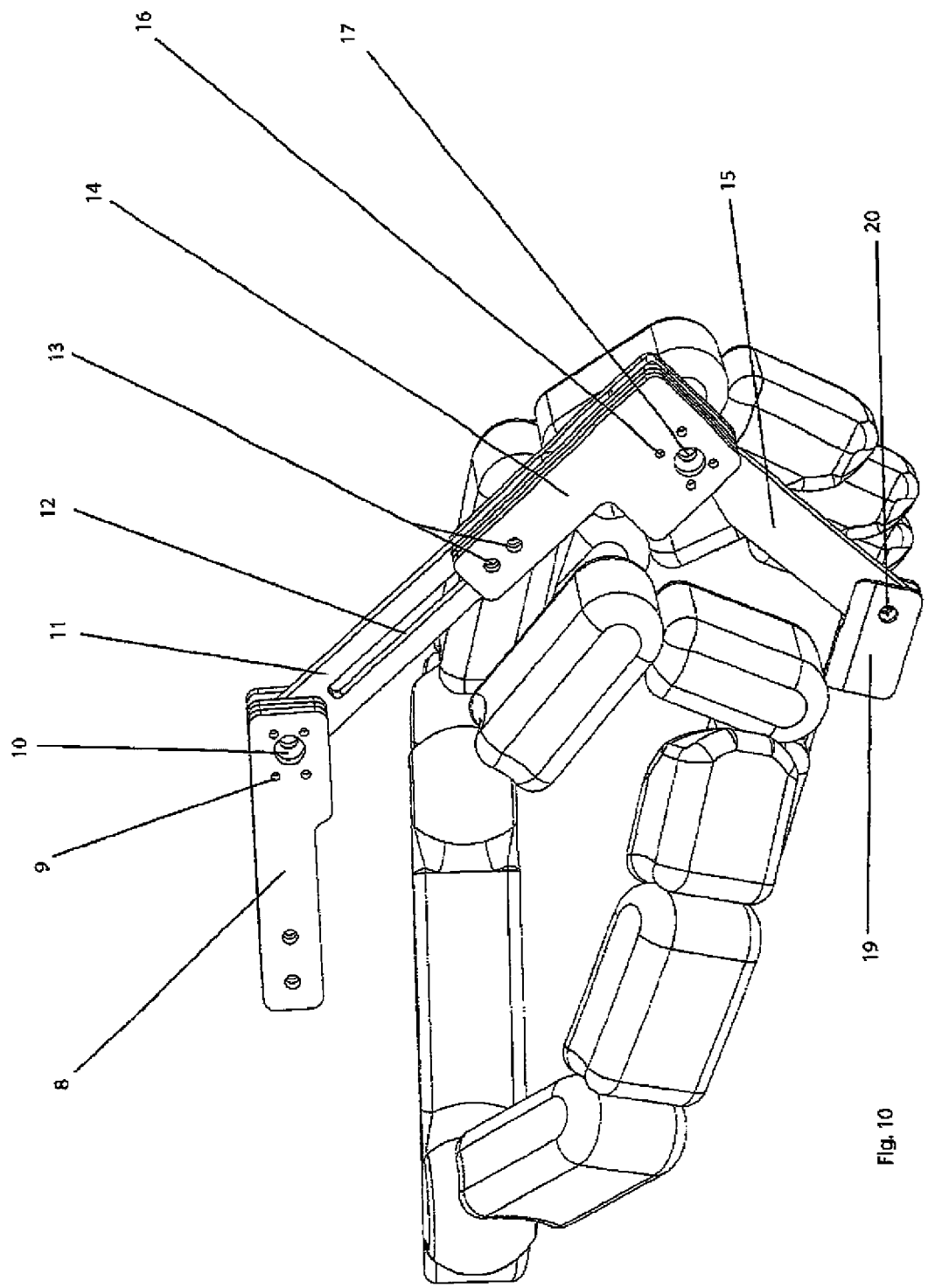

With further bending of the finger as shown in FIGS. 8-10 the third linkage 15 and the fourth linkage 19 first further develop into a more or less straight angular orientation with reference to each other as shown in FIG. 9 and enabled by the second joint 17 and the third joint 20. Eventually the rotation along joint 20 continues to enable that the most forward phalange of the index finger is enabled to occupy a position pointing to the inner palm of the user's hand 1.

Although the invention has been discussed in the foregoing with reference to an exemplary embodiment of the exoskeleton glove of the invention, the invention is not restricted to this particular embodiment which can be varied in many ways without departing from the invention. The discussed exemplary embodiment shall therefore not be used to construe the appended claims strictly in accordance therewith. On the contrary the embodiment is merely intended to explain the wording of the appended claims without intent to limit the claims to this exemplary embodiment. The scope of protection of the invention shall therefore be construed in accordance with the appended claims only, wherein a possible ambiguity in the wording of the claims shall be resolved using this exemplary embodiment.

What is claimed is:

1. A linkage mechanism for an individual finger of an exoskeleton glove, the linkage mechanism comprising:
   a first linkage attachable to the exoskeleton glove,
   a second linkage connected to the first linkage through a first joint, a third linkage connected to the second linkage through a second joint, and a fourth linkage connected to the third linkage through a third joint, wherein the fourth linkage is provided with a finger orthosis, and the second linkage, the third linkage and the fourth linkage are capable to assume a mutually parallel placement wherein the finger orthosis is adjacent to the second joint at a farthest end from the exoskeleton glove, and the third joint is closer to the exoskeleton glove than the second joint, and wherein each of the first, second and third joint is a rotary joint, wherein each of the first, second and third joints are mounted in a fixed position with respect to the respective linkages it is mounted to such that the rotary joints are configured to fold and unfold the linkage mechanism.

2. The linkage mechanism of claim 1, wherein the second linkage is extendable.

3. The linkage mechanism of claim 1, wherein the second linkage has a first portion which is embodied with a slide, and a second portion which is provided with a slider that is movable in the slide so as to arrange that the linkage mechanism is capable to be attuned to a user's finger length.

4. The linkage mechanism of claim 3, wherein the slider is lockable in the slide.

5. The linkage mechanism of claim 1, wherein the first joint is provided with a sensor for measuring angular displacement of the first and second linkages.

6. The linkage mechanism of claim 1, wherein the first joint is spring-loaded with a spring for resisting or supporting angular displacement of the first and second linkages.

7. The exoskeleton glove comprising the linkage mechanism of claim 1 for each finger and thumb of the exoskeleton glove, wherein each linkage mechanism is provided with an intermediate linkage or linkages between the first linkage and the glove that indirectly attaches the first linkage to the glove.

8. The exoskeleton glove of claim 7, wherein the intermediate linkage or linkages are each provided with one or more joints to enable movements of the linkage mechanism for the thumb according to a user's carpalmetacarpal joint.

9. The linkage mechanism of claim 1, wherein the second joint is provided with a sensor for measuring angular displacement of the second and third linkages.

10. The linkage mechanism of claim 1, wherein the second joint is spring-loaded with a spring for resisting or supporting angular displacement of the second and third linkages.

* * * * *